United States Patent [19]

Kühle et al.

[11] 4,382,956

[45] May 10, 1983

[54] COMBATING FUNGI WITH N-SULPHENYLATED BIURETS

[75] Inventors: Engelbert Kühle, Bergisch-Gladbach; Volker Paul, Solingen; Wilhelm Brandes, Leichlingen, all of Fed. Rep. of Germany

[73] Assignee: Bayer Aktiengesellschaft, Leverkusen, Fed. Rep. of Germany

[21] Appl. No.: 331,098

[22] Filed: Dec. 15, 1981

[30] Foreign Application Priority Data

Dec. 30, 1980 [DE] Fed. Rep. of Germany ....... 3049439

[51] Int. Cl.$^3$ .................... C07C 127/24; A61K 31/17
[52] U.S. Cl. .................... 424/322; 424/249; 424/285; 544/211; 544/213; 564/38; 549/480; 549/493; 549/448
[58] Field of Search .................. 260/347.2; 424/249, 424/285, 322; 544/211, 213; 564/38

[56] References Cited

FOREIGN PATENT DOCUMENTS 1472975 9/1965 France .
842091 7/1960 United Kingdom .................. 564/38

OTHER PUBLICATIONS

Chemische Berichte, 99 Jahrg. Nr. 10, pp. 3063, 3103–3107, 1966.

*Primary Examiner*—Thomas A. Waltz
*Attorney, Agent, or Firm*—Sprung, Horn, Kramer & Woods

[57] ABSTRACT

N-Sulphenylated biurets of the formula $$R^1-S-N(R^2)-CO-NH-CO-N(R^3)(R^4)$$

in which

R$^1$ represents a trihalogenomethyl radical,

R$^2$ represents an optionally substituted aliphatic, cycloaliphatic, araliphatic or aromatic radical and R$^3$ and R$^4$ are identical or different and represent a hydrogen atom, an optionally substituted aliphatic, cycloaliphatic, araliphatic, aromatic or heterocyclic radical or the amino or hydroxyl group, or together with the connecting nitrogen atom represent a five-membered or six-membered heterocyclic ring, the ring carbon atoms of which are optionally interrupted by one or more further heteroatoms, which possess fungicidal activity.

12 Claims, No Drawings

COMBATING FUNGI WITH N-SULPHENYLATED BIURETS

Type Ib The invention relates to certain new N-sulphenylated biurets, to processes for their production and to their use as fungicides.

It has been known for a long time that N-trihalogenomethylthio compounds can be used as fungicides in agriculture. Thus, for example, N-(trichloromethylthio)-tetrahydrophthalimide and N,N-dimethyl-N'-phenyl-N'-(fluorodichloromethylthio)-sulphamide are used in practice for combating fungal diseases in fruit growing and viticulture (see German Pat. No. 887,506 (1950) and Angew. Chem. 76, 807 (1964)). However, their action in tropical crops, for example in rice, is inadequate.

The present invention now provides, as new compounds, the N-sulphenylated biurets of the general formula

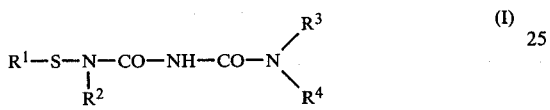

in which
R$^1$ represents a trihalogenomethyl radical,
R$^2$ represents an optionally substituted aliphatic, cycloaliphatic, araliphatic or aromatic radical and
R$^3$ and R$^4$ are identical or different and represent a hydrogen atom, an optionally substituted aliphatic, cycloaliphatic, araliphatic, aromatic or heterocyclic radical or the amino or hydroxyl group, or together with the connecting nitrogen atom represent a five-membered or six-membered heterocyclic ring, the ring carbon atoms of which are optionally interrupted by one or more further hetero-atoms, such as nitrogen, oxygen or sulphur.

According to the present invention there is further provided a process for the production of a compound of the present invention, characterized in that
(a) a N-(sulphenamido)-acyl isocyanate of the general formula

in which
R$^1$ and R$^2$ have the abovementioned meanings, is reacted with an amine of the general formula

in which
R$^3$ and R$^4$ have the abovementioned meanings, if appropriate in the presence of a diluent, or
(b) a N-sulphenylated allophanic acid phenyl ester of the formula

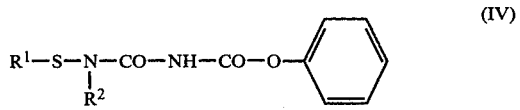

in which
R$^1$ and R$^2$ have the abovementioned meaning, is reacted with an amine of the general formula (III), as defined above, if appropriate in the presence of a diluent.

The new N-sulphenylated biurets of the present invention have powerful fungicidal properties.

Surprisingly, the N-sulphenylated biurets according to the invention have a more powerful fungicidal action in various crops, such as in rice, than the known trihalogenomethylthio compounds. They thus represent an enrichment of the art.

Preferred compounds according to the present invention are those in which:
R$^1$ represents a trichloromethyl or fluorodichloromethyl group,
R$^2$ represents an aliphatic radical which has 1 to 6 carbon atoms and is optionally interrupted by a heteroatom (for example oxygen or sulphur) and is optionally halogenated, a cycloaliphatic radical with 5 to 8 carbon atoms, an araliphatic radical which has 7 to 10 carbon atoms and in which the aromatic part is optionally substituted by halogen, nitro, alkyl with 1 to 4 carbon atoms and/or trifluoromethyl, or an aromatic radical which has 6 to 10 ring carbon atoms and is optionally substituted by halogen, nitro, alkyl with up to 4 carbon atoms and/or trifluoromethyl, and
R$^3$ and R$^4$ independently represent a hydrogen atom, a saturated or unsaturated aliphatic radical which has 1 to 6 carbon atoms and is optionally halogenated, and interrupted by hetero-atoms (such as oxygen, sulphur or nitrogen), a cycloaliphatic radical which has 5 to 7 ring carbon atoms and is optionally substituted by alkyl with 1 to 4 carbon atoms, or an araliphatic radical which has 7 to 10 carbon atoms and in which the aromatic part is optionally substituted by halogen, nitro, alkyl with 1 to 4 carbon atoms and/or by trifluoromethyl, or an aromatic radical which has 6 to 10 ring carbon atoms and is optionally substituted by halogen, nitro, alkyl with 1 to 4 carbon atoms and/or by trifluoromethyl, or a heterocyclic radical which has 5 to 7 ring atoms and in which oxygen, sulphur and/or nitrogen can be present as hetero-atoms, it also being possible for this heterocyclic radical to be bonded to the nitrogen atom which carries the R$^3$ and R$^4$ substituents via a —CH$_2$— group, or, finally, the amino or hydroxyl group.

Very particularly preferred compounds of the present invention are those in which:
R$^1$ represents a trichloromethyl or fluorodichloromethyl group,
R$^2$ represents an alkyl group which has 1 to 4 carbon atoms and is optionally substituted by methoxy or ethoxy, or cyclohexyl or phenyl,
R$^3$ represents a hydrogen atom, an alkyl group with up to 6 carbon atoms or an alkenyl group with up to 4 carbon atoms, a halogenoalkyl group with up to 4 carbon atoms and up to 5 halogen atoms, or phenyl, halogenophenyl, cyclohexyl, a furfuryl group or a triazine group, it being possible for the latter to be further substituted by methyl groups, or represents an amino group, and $R^4$ represents a hydrogen atom or an alkyl group with up to 6 carbon atoms.

If, for example, for the preparation of the compounds according to the present invention, N-(fluorodichloromethylsulphenyl)-N-methylcarbamoyl isocyanate is used as the starting component according to reaction variant (a) or N-(fluorodichloromethylsulphenyl)-N-methyl-allophanic acid phenyl ester is used as the starting component according to reaction variant (b) and in both cases ethylamine is used as the starting component, the course of the reaction can be represented by the following equations:

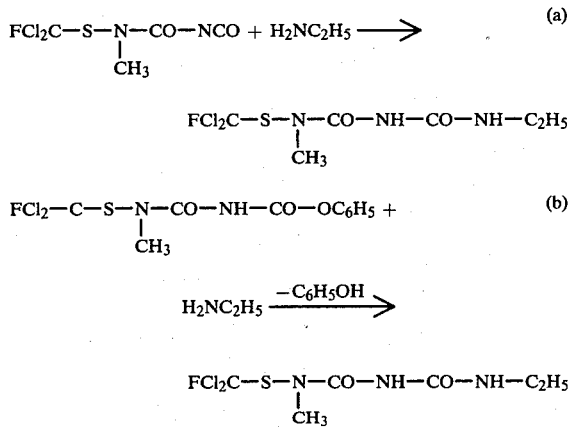

Preferred N-(sulphenamido)-acyl isocyanates of formula (II) required as starting substances for reaction variant (a) are those in which $R^1$ and $R^2$ have the meanings which have already been mentioned for these substituents in the discussion of the preferred and particularly preferred compounds according to the present invention.

The compounds of the formula (II) are novel; they are the subject of copending Application Ser. No. 329,961 filed 12/11/81 now U.S. Pat. No. 4,376,735. They are obtained when a trihalogenomethane-sulphenamide of the general formula

in which:

$R^1$ and $R^2$ have the abovementioned meanings, is reacted with chlorocarbonyl isocyanate of the formula Cl—CO—NCO                    (VI)

if appropriate in the presence of a diluent, in the temperature range between 0° and 150° C.

N-(Sulphenamido)-acyl isocyanates of the formula (II) which are suitable for reaction variant (a) are the acyl isocyanates of N-(trichloromethylsulphenyl)-, N-(fluorodichloromethylsulphenyl)- and N-(trifluoromethylsulphenyl)-methylamine, -isopropylamine, -2-methoxyethylamine, -tert.-butylamine, -cyclopentylamine, -cyclohexylamine, -benzylamine, -4-chlorobenzylamine, -phenethylamine, -aniline, -3-trifluoromethylaniline, -3,4-dichloroaniline, -4-anisidine, -3-toluidine, -2-aminopyridine and -2-furylamine.

The precursors of the formula (V) are known (see French Patent Specification 1,339,765 and Chem. Abstr. 60, 5519 (1964)); they are obtained when a trihalogenomethanesulphenyl chloride is reacted with a primary amine, for example in toluene as a solvent, in the temperature range between +20° and 30° C. The precursor of the formula (VI) is likewise known (see Angew. Chem. 89, 789 (1977)), and is obtained by partial hydrolysis of the addition adduct of phosgene and cyanogen chloride.

Preferred N-sulphenylated allophanic phenyl esters of formula (IV) required as starting materials for reaction variant (b) are those in which $R^1$ and $R^2$ have the meanings given in the description of the preferred and particularly preferred compounds of the present invention.

The compounds of formula (IV) are obtained when phenoxycarbonyl isocyanate of the formula

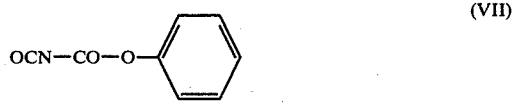

is added onto the abovementioned trihalogenomethanesulphenamides of the formula (V) (see also the preparative examples hereinbelow).

Preferred amines of formula (III) required for the reaction variants (a) and (b) are those in which the substituents $R^3$ and $R^4$ have the meanings which have already been mentioned as for these substituents in the discussion of the preferred and particularly preferred compounds of the present invention. The compounds are generally known. Examples which may be mentioned are ammonia, methyl-, dimethyl-, ethyl-, isopropyl-, allyl-, trifluoroethyl-, methoxyethyl-, tert.-butyl-, cyclopentyl-, 2-methylcyclohexylamin and 4-chloroaniline, 4-fluoroaniline, 3-anisidine, 1-naphthylamine, 2-aminopyridine, 2-aminothiophene and 2-aminofuran.

Possible diluents in carrying out the preparation according to reaction variant (a) are any of the inert organic solvents. These include, preferably, hydrocarbons, such as benzine, benzene or toluene, ethers, such as diethyl ether, and ketones, such as acetone and methyl ethyl ketone.

Reaction temperatures can be varied within a substantial range in reaction variant (a). In general, the reaction is carried out at a temperature between $-10°$ and $+100°$ C., preferably between $+20°$ and 50° C.

In carrying out the reaction according to reaction variant (a), about 1 mol of the amine of the formula (III) is employed per mol of N-(sulphenamido)-acyl isocyanate of the formula (II). The compounds according to the invention are in general isolated by crystallisation.

In carrying out the reaction variant (b), the N-sulphenylated allophanic acid phenyl ester of the formula (IV) is generally dissolved in a solvent in which the end product is sparingly soluble, preferably in a $C_1$ to $C_6$ aliphatic alcohol or in an aqueous mixture thereof, prior to the reaction with the amine of formula (III). The product is thereby easily separated off from the phenol formed in the reaction. This reaction is generally carried out at $-10°$ to $+100°$ C., preferably at $+10°$ to 50° C.

Preferably the N-sulphenylated allophanic acid phenyl ester of the formula (IV), dissolved in a $C_1$ to $C_6$ alcohol, is initially introduced into the reaction vessel, and at least the equimolar amount of the amine (III), if appropriate in aqueous or alcoholic solution, is added. The end product of the formula (I) crystallizes out and is separated off in the customary manner.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes, and Deuteromycetes.

As plant protection agents, the active compounds can be used with particularly good success for combating *Pyricularia oryzae*, the causative organism of Brusone disease, and *Pellicularia sasakii*, the causative organism of leaf sheath blight in rice. Good successes are also achieved against apple scab (*Venturia inaequalis*) and grey mould (*Botrytis cinerea*).

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, in formulations used with burning equipment, such as fumigating cartridges, fumigating cans, fumigating coils and the like, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

Especially in the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.001 to 0.02%, are required at the place of action.

The present invention also provides fungicidal compositions containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

PREPARATIVE EXAMPLES
EXAMPLE 1

(a) Preparation of the precursors

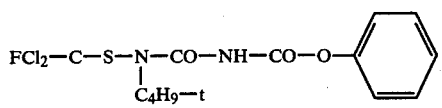 (VI)

62 g (0.3 mol) of N-(fluorodichloromethanesulphenyl)-tert.-butylamide (boiling point $_1$60°–65° C.), which had been prepared from fluorodichloromethanesulphenyl chloride and tert.-butylamine and was dissolved in 30 ml of toluene, were added dropwise, at room temperature, to 48.8 g (0.3 mol) of phenoxycarbonyl isocyanate, dissolved in 150 ml of dry toluene. During this addition, the temperature rose to 44° C. 39 g of the above compound of melting point 101° to 102° C. crystallized out in the cold. A further 34 g of the product could be obtained from the mother liquor by the addition of petroleum ether.

The following precursors were obtained in a similar manner.

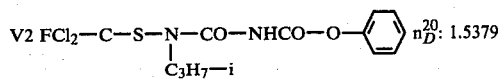

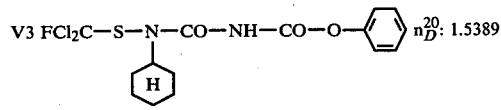

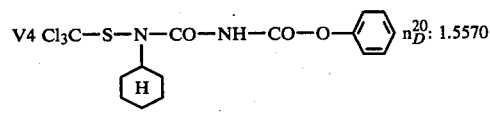

(b) (Reaction variant a)

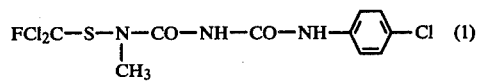 (1)

8.2 g (0.035 mol) of N-(fluorodichloromethanesulphenyl)-N-(methyl)-amidocarbonyl isocyanate were dissolved in 60 ml of acetone, and the solution was reacted with a solution of 4.5 g (0.035 mol) of 4-chloroaniline in 20 ml of acetone at room temperature. During this reaction, the temperature rose to 34° C. When water was added to the mixture, 7 g of 1-fluorodichloromethylthio-1-methyl-5-(4-chlorophenyl)-biuret of melting point 148° C. were obtained, that is to say 55% of theory.

EXAMPLE 2

(Reaction variant b)

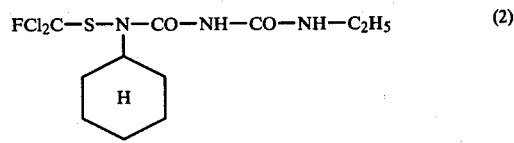 (2)

39.5 g (0.1 mol) of N-(fluorodichloromethylsulphenyl)-N-(cyclohexyl)-allophanic acid phenyl ester were dissolved in 50 ml of methanol, and 15 ml of 50% strength aqueous ethylamine solution were added at 10° to 20° C., whilst cooling with ice-water. During this addition, the reaction product crystallized. The product was filtered off and dissolved in 30 ml of hot methanol, and 15 ml of water were added at 50° C. The reaction product, which precipitated in the cold, was filtered off and dried. 26 g of 1-fluorodichloromethylthio-1-cyclohexyl-5-ethyl-biuret of melting point 104°–105° C. were obtained, that is to say 75% of theory.

The following compounds of the general formula

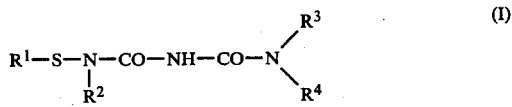 (I)

could be obtained in an analogous manner:

TABLE

| Compound No. | $R^1$ | $R^2$ | $R^3$ | $R^4$ | Melting point (°C.) or refractive index |
|---|---|---|---|---|---|
| 3 | CCl$_3$ | C$_4$H$_9$—n | CH$_3$ | CH$_3$ | 78 |
| 4 | CCl$_3$ | C$_4$H$_9$—n | C$_2$H$_5$ | H | 48 |
| 5 | CCl$_3$ | C$_4$H$_9$—n | —⟨phenyl⟩ | H | 83 |
| 6 | CCl$_3$ | —⟨cyclohexyl-H⟩ | CH$_3$ | H | 110 |
| 7 | CCl$_3$ | —⟨cyclohexyl-H⟩ | C$_2$H$_5$ | H | 108 |
| 8 | CCl$_3$ | —⟨cyclohexyl-H⟩ | C$_3$H$_7$—i | H | 86 |

TABLE-continued

| Compound No. | R¹ | R² | R³ | R⁴ | Melting point (°C.) or refractive index |
|---|---|---|---|---|---|
| 9 | CCl₃ | —C₆H₅ (phenyl) | —C₆H₅ (phenyl) | H | 125 |
| 10 | CCl₂F | CH₃ | CH₃ | H | 102 |
| 11 | CCl₂F | CH₃ | C₂H₅ | H | 65 |
| 12 | CCl₂F | CH₃ | C₃H₇—n | H | 48 |
| 13 | CCl₂F | CH₃ | CH₂—CH=CH₂ | H | 57 |
| 14 | CCl₂F | CH₃ | C₃H₇—i | H | 89 |
| 15 | CCl₂F | CH₃ | C₄H₉—t | H | 83 |
| 16 | CCl₂F | CH₃ | —C₆H₁₁ (cyclohexyl) | H | 117 |
| 17 | CCl₂F | CH₃ | —C₆H₅ (phenyl) | H | 138 |
| 18 | CCl₂F | C₃H₇—i | C₂H₅ | H | 82 |
| 19 | CCl₂F | C₃H₇—i | —C₆H₁₁ (cyclohexyl) | H | 89 |
| 20 | CCl₂F | C₄H₉—t | CH₃ | H | 87 |
| 21 | CCl₂F | C₄H₉—t | C₂H₅ | H | 86 |
| 22 | CCl₂F | C₄H₉—t | —C₆H₁₁ (cyclohexyl) | H | 111 |
| 23 | CCl₂F | —C₆H₅ (phenyl) | C₂H₅ | H | 109 |
| 24 | CCl₂F | —C₆H₅ (phenyl) | —C₆H₁₁ (cyclohexyl) | H | 109 |
| 25 | CCl₂F | —C₆H₁₁ (cyclohexyl) | CH₃ | CH₃ | 117 |
| 26 | CCl₂F | —C₆H₁₁ (cyclohexyl) | H | H | 153 |
| 27 | CCl₂F | —C₆H₁₁ (cyclohexyl) | C₃H₇—i | H | 80 |
| 28 | CCl₂F | —C₆H₁₁ (cyclohexyl) | —C₆H₁₁ (cyclohexyl) | H | 131 |
| 29 | CCl₂F | —C₆H₁₁ (cyclohexyl) | C₄H₉—t | H | 108 |
| 30 | CCl₂—F | —C₆H₁₁ (cyclohexyl) | CH₂—C(CH₃)₃ | H | 134 |
| 31 | CCl₂—F | —C₆H₁₁ (cyclohexyl) | CH₂—(furan-2-yl) | H | 86 |
| 32 | CCl₂—F | —C₆H₁₁ (cyclohexyl) | —C₆H₄—Cl | H | 155 |
| 33 | CCl₂F | CH₃ | —C₆H₄—Cl | H | 148 |
| 34 | CCl₂F | CH₂—CH₂—OCH₃ | C₃H₇—i | H | |

TABLE-continued

| Compound No. | $R^1$ | $R^2$ | $R^3$ | $R^4$ | Melting point (°C.) or refractive index |
|---|---|---|---|---|---|
| 35 | $CCl_2F$ | —C₆H₁₁ | $CH_2$—$CF_3$ | $CH_3$ | 84–85 |
| 36 | $CCl_2F$ | —C₆H₁₁ | $CH_2$—$CF_3$ | H | $n_D^{20}$: 1.5001 |
| 37 | $CCl_2F$ | —C₆H₁₁ | $CH_2$—$CH_2$—$CF_3$ | H | 105 |
| 38 | $CCl_2F$ | —C₆H₁₁ | $CH$—$CF_3$ \| $CH_3$ | H | 140 |
| 39 | $CCl_2F$ | —C₆H₁₁ | $CH_2$—$CH_2$—$CFCl_2$ | H | $n_D^{20}$: 1.5177 |
| 40 | $CCl_2F$ | —C₆H₁₁ | $CH_2$—$CF_3$ | $C_2H_5$ | $n_D^{20}$: 1.4918 |
| 41 | $CCl_2F$ | $C_4H_9$—t | $NH_2$ | H | 125–126 |
| 42 | $CCl_2F$ | $C_3H_7$—i | $C_4H_9$—t | H | $n_D^{20}$: 1.5012 |
| 43 | $CCl_2F$ | $C_3H_7$—i | $NH_2$ | H | 130 |
| 44 | $CCl_2F$ | $C_4H_9$—n | 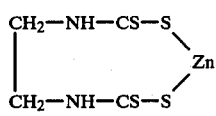 | H | 126–129 |
| 45 | $CCl_2F$ | —C₆H₁₁ | $NH_2$ | H | 119–121 |
| 46 | $CCl_2F$ | —C₆H₁₁ | $CH_3$ | H | 107–109 |
| 47 | $CCl_2F$ | —C₆H₅ | —C₆H₅ | H | 139–141 |

The fungicidal activity of the compounds of this invention is illustrated by the following biotest examples wherein the compounds according to the present invention are each identified by the number (given in brackets) from Examples 1 and 2 and the table.

The known comparison compound is identified as follows:

$$\begin{array}{c} CH_2-NH-CS-S \\ | \qquad\qquad\qquad\diagdown Zn \\ CH_2-NH-CS-S \diagup \end{array}$$

EXAMPLE 3

Pyricularia test (rice)/protective
Solvent: 12.5 parts by weight of acetone
Emulsifier: 0.3 part by weight of alkylaryl polyglycol ether To produce a suitable preparation of active compound, 1 part by weight of active compound was mixed with the stated amount of solvent, and the concentrate was diluted with water and the stated amount of emulsifier, to the desired concentration.

To test for protective activity, young rice plants were sprayed with the preparation of active compound until dripping wet. After the spray coating had dried off, the plants were inoculated with an aqueous spore suspension of Pyricularia oryzae. The plants were then placed in a greenhouse at 100% relative atmospheric humidity and 25° C.

Evaluation of the disease infestation was carried out 4 days after the inoculation.

In this test, a clearly superior activity compared with the prior art was shown, for example, by the compounds (2) and (29).

EXAMPLE 4

Pellicularia test (rice)
Solvent: 12.5 parts by weight of acetone
Emulsifier: 0.3 parts by weight of alkylaryl polyglycol ether To produce a suitable preparation of active compound, 1 part by weight of active compound was mixed with the stated amount of solvent, and the concentrate was diluted with water and the stated amount of emulsifier, to the desired concentration.

To test for activity, young rice plants in the 3 to 4 leaf stage were sprayed until dripping wet. The plants were then inoculated with *Pellicularia sasakii* and were placed at 25° C. and 100% relative atmospheric humidity.

The evaluation of the disease infestation was carried out 5 to 8 days after the inoculation.

In this test, a clearly superior activity compared with the prior art was shown, for example, by the compounds (2) and (29).

EXAMPLE 5

Botrytis test (beans)/protective
Solvent: 4.7 parts by weight of acetone
Dispersing agent: 0.3 part by weight of alkylaryl polyglycol ether
Water: 95 parts by weight.

The amount of active compound required to give the desired concentration of active compound in the spray liquid was mixed with the stated amount of the solvent and the concentrate was diluted with the stated amount of water which contained the stated additives.

*Phaseolus vulgaris* plants in the 2-leaf stage were sprayed with the spray liquid until dripping wet. After 24 hours, 2 small pieces of agar covered with *Botrytis cinerea* were placed on each leaf. The inoculated plants were placed in a darkened, moist chamber at 20° C. 3 days after the inoculation, the size of the infected spots on the leaves was rated.

The ratings were converted to percent infection. 0% denoted no infection and 100% denoted that the plants were completely infected.

In this test, a clearly superior activity compared with the prior art was shown, for example, by the compounds (45), (46), (17), (16) and (47).

It will be appreciated that the instant specification and examples are set forth by way of illustration and not limitation, and that various modifications and changes may be made without departing from the spirit and scope of the present invention.

We claim:

1. An N-sulphenylated biuret of the formula

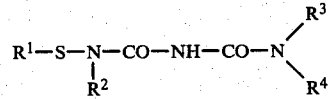

in which
R$^1$ represents a trihalogenomethyl radical,
R$^2$ represents an optionally substituted aliphatic, cycloaliphatic, araliphatic or aromatic radical and
R$^3$ and R$^4$ are identical or different and represent a hydrogen atom, an optionally substituted aliphatic, cycloaliphatic, araliphatic, aromatic or heterocyclic radical or the amino or hydroxyl group, or together with the connecting nitrogen atom represent a five-membered or six-membered heterocyclic ring, the ring carbon atoms of which are optionally interrupted by one or more further hetero-atoms.

2. A compound according to claim 1, in which R$^3$ and R$^4$ together with the connecting nitrogen atom represent a five-membered or six-membered heterocyclic ring, the ring carbon atoms of which are interrupted by one or more of nitrogen, oxygen and sulphur atoms.

3. A compound according to claim 1, in which
R$^1$ represents a trichloromethyl or fluorodichloromethyl group,
R$^2$ represents an aliphatic radical which has 1 to 6 carbon atoms and is optionally interrupted by a hetero-atom and is optionally halogenated, a cycloaliphatic radical with 5 to 8 carbon atoms, an araliphatic radical which has 7 to 10 carbon atoms and in which the aromatic part is optionally substituted by halogen, nitro, alkyl with 1 to 4 carbon atoms and/or trifluoromethyl, or an aromatic radical which has 6 to 10 ring carbon atoms and is optionally substituted by halogen, nitro, alkyl with up to 4 carbon atoms and/or trifluoromethyl, and
R$^3$ and R$^4$ independently represent a hydrogen atom, a saturated or unsaturated aliphatic radical which has 1 to 6 carbon atoms and is optionally halogenated, and interrupted by hetero-atoms, a cycloaliphatic radical which has 5 to 7 ring carbon atoms and is optionally substituted by alkyl with 1 to 4 carbon atoms, or an araliphatic radical which has 7 to 10 carbon atoms and in which the aromatic part is optionally substituted by halogen, nitro, alkyl with 1 to 4 carbon atoms, and/or by trifluoromethyl, or an aromatic radical which has 6 to 10 ring carbon atoms and is optionally substituted by halogen, nitro, alkyl with 1 to 4 carbon atoms and/or by trifluoromethyl, or a heterocyclic radical which has 5 to 7 ring atoms and in which oxygen, sulphur and/or nitrogen can be present as heteroatoms, it also being possible for this heterocyclic radical to be bonded to the nitrogen atom which carries the R$^3$ and R$^4$ substituents via a —CH$_2$— group, or finally the amino or hydroxyl group.

4. A compound according to claim 1, in which
R$^1$ represents a trichloromethyl or fluorodichloromethyl group,
R$^2$ represents an alkyl group which has 1 to 4 carbon atoms and is optionally substituted by methoxy or ethoxy, or cyclohexyl or phenyl,
R$^3$ represents a hydrogen atom, an alkyl group with up to 6 carbon atoms or an alkenyl group with up to 4 carbon atoms, a halogenoalkyl group with up to 4 carbon atoms and up to 5 halogen atoms, or phenyl, halogenophenyl, cyclohexyl, a furfuryl group or a triazine group, it being possible for the latter to be further substituted by methyl groups, or represents an amino group, and
R$^4$ represents a hydrogen atom or an alkyl group with up to 6 carbon atoms.

5. A compound according to claim 1, wherein such compound is 1-fluorodichloromethylthio-1-cyclohexyl-5-ethyl-biuret of the formula

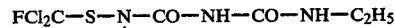

6. A compound according to claim 1, wherein such compound is 1-fluorodichloromethylthio-1-isopropyl-5-cyclohexyl-biuret of the formula

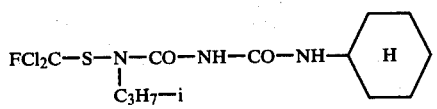

7. A compound according to claim 1, wherein such compound is 1-fluorodichloromethylthio-1-cyclohexyl-5-isopropyl-biuret of the formula

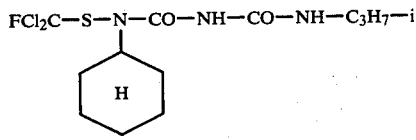

8. A compound according to claim 1, wherein such compound is 1-fluorodichloromethylthio-1-cyclohexyl-5-t-butyl-biuret of the formula

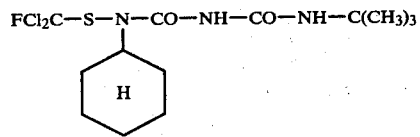

9. A compound according to claim 1, wherein such compound is 1-fluorodichloromethylthio-1-cyclohexyl-5-methyl-biuret of the formula

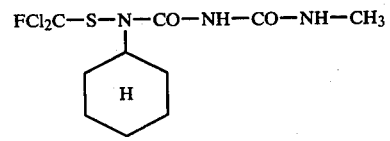

10. A fungicidal composition comprising as active ingredient a fungicidally effective amount of a compound according to claim 1 in admixture with a diluent.

11. A method of combating fungi comprising applying to the fungi or to a habitat thereof, a fungicidally effective amount of a compound according to claim 1.

12. The method according to claim 11, wherein such compound is
1-fluorodichloromethylthio-1-cyclohexyl-5-ethyl-biuret,
1-fluorodichloromethylthio-1-isopropyl-5-cyclohexyl-biuret,
1-fluorodichloromethylthio-1-cyclohexyl-5-isopropyl-biuret,
1-fluorodichloromethylthio-1-cyclohexyl-5-t-butyl-biuret or
1-fluorodichloromethylthio-1-cyclohexyl-5-methyl-biuret.

* * * * *